(12) United States Patent
Swedek et al.

(10) Patent No.: US 7,016,795 B2
(45) Date of Patent: Mar. 21, 2006

(54) SIGNAL IMPROVEMENT IN EDDY CURRENT SENSING

(75) Inventors: Boguslaw A. Swedek, Cupertino, CA (US); Manoocher Birang, Los Gatos, CA (US)

(73) Assignee: Applied Materials Inc., Santa Clara, CA (US)

( * ) Notice: Subject to any disclaimer, the term of this patent is extended or adjusted under 35 U.S.C. 154(b) by 314 days.

(21) Appl. No.: 10/359,107

(22) Filed: Feb. 4, 2003

(65) Prior Publication Data

US 2004/0152310 A1 Aug. 5, 2004

(51) Int. Cl.
*G06F 19/00* (2006.01)
*G01B 7/06* (2006.01)

(52) U.S. Cl. .................. 702/64; 702/97; 702/170; 324/229; 324/228; 324/230

(58) Field of Classification Search .................. 702/64, 702/97, 170; 324/229, 230, 228; 156/345.12, 156/345.13, 345.15, 345.24, 345.25
See application file for complete search history.

(56) References Cited

U.S. PATENT DOCUMENTS

| | | | |
|---|---|---|---|
| 4,005,359 A | 1/1977 | Smoot | |
| 4,112,365 A | 9/1978 | Larson et al. | |
| 4,303,885 A | 12/1981 | Davis et al. | |
| 4,467,281 A | 8/1984 | Davis et al. | |
| 4,556,845 A | 12/1985 | Strope et al. | |
| 4,715,007 A | 12/1987 | Fujita et al. | |
| 4,716,366 A | 12/1987 | Hosoe et al. | |
| 4,829,251 A | 5/1989 | Fischer | |
| 4,849,694 A | 7/1989 | Coates | |
| 5,003,262 A | 3/1991 | Egner et al. | |
| 5,096,754 A | 3/1992 | Hammer et al. | |
| 5,213,655 A | 5/1993 | Leach et al. | |
| 5,237,271 A | 8/1993 | Hedengren | |
| 5,343,146 A | 8/1994 | Koch et al. | |
| 5,355,083 A * | 10/1994 | George et al. | 324/229 |
| 5,433,651 A | 7/1995 | Lustig et al. | |
| 5,525,903 A | 6/1996 | Mandl et al. | |
| 5,541,510 A * | 7/1996 | Danielson | 324/233 |
| 5,559,428 A | 9/1996 | Li et al. | |
| 5,644,221 A | 7/1997 | Li et al. | |
| 5,660,672 A | 8/1997 | Li et al. | |
| RE35,703 E | 12/1997 | Koch et al. | |
| 5,731,697 A | 3/1998 | Li et al. | |
| 5,893,796 A | 4/1999 | Birang et al. | |
| 6,068,539 A | 5/2000 | Bajaj et al. | |

(Continued)

FOREIGN PATENT DOCUMENTS

EP 0 460 348 A2 12/1991

(Continued)

*Primary Examiner*—Patrick J. Assouad
(74) *Attorney, Agent, or Firm*—Fish & Richardson

(57) ABSTRACT

Improved endpoint detection and/or thickness measurements may be obtained by correcting sensor data using calibration parameters and/or drift compensation parameters. Calibration parameters may include an offset and a slope, or other parameters. Drift compensation parameters may include off-wafer measurements.

22 Claims, 11 Drawing Sheets

U.S. PATENT DOCUMENTS

| | | | |
|---|---|---|---|
| 6,086,734 A * | 7/2000 | Harada | 204/298.03 |
| 6,254,459 B1 | 7/2001 | Bajaj et al. | |
| 6,549,006 B1 * | 4/2003 | Le | 324/230 |
| 6,563,308 B1 * | 5/2003 | Nagano et al. | 324/230 |
| 6,741,076 B1 * | 5/2004 | Le | 324/230 |
| 6,762,604 B1 * | 7/2004 | Le | 324/230 |
| 6,808,590 B1 * | 10/2004 | Gotkis et al. | 156/345.16 |
| 2001/0008827 A1 | 7/2001 | Kimura et al. | |
| 2002/0053904 A1 | 5/2002 | Chen et al. | |
| 2002/0077031 A1 | 6/2002 | Johansson et al. | |
| 2003/0067298 A1 * | 4/2003 | Nagano et al. | 324/230 |
| 2003/0206008 A1 * | 11/2003 | Le | 324/230 |
| 2003/0206009 A1 * | 11/2003 | Le | 324/230 |
| 2003/0210041 A1 * | 11/2003 | Le | 324/230 |
| 2005/0017712 A1 * | 1/2005 | Le | 324/230 |
| 2005/0072528 A1 * | 4/2005 | Owczarz et al. | 156/345.16 |

FOREIGN PATENT DOCUMENTS

| | | |
|---|---|---|
| EP | 1 116 552 A2 | 7/2001 |

* cited by examiner

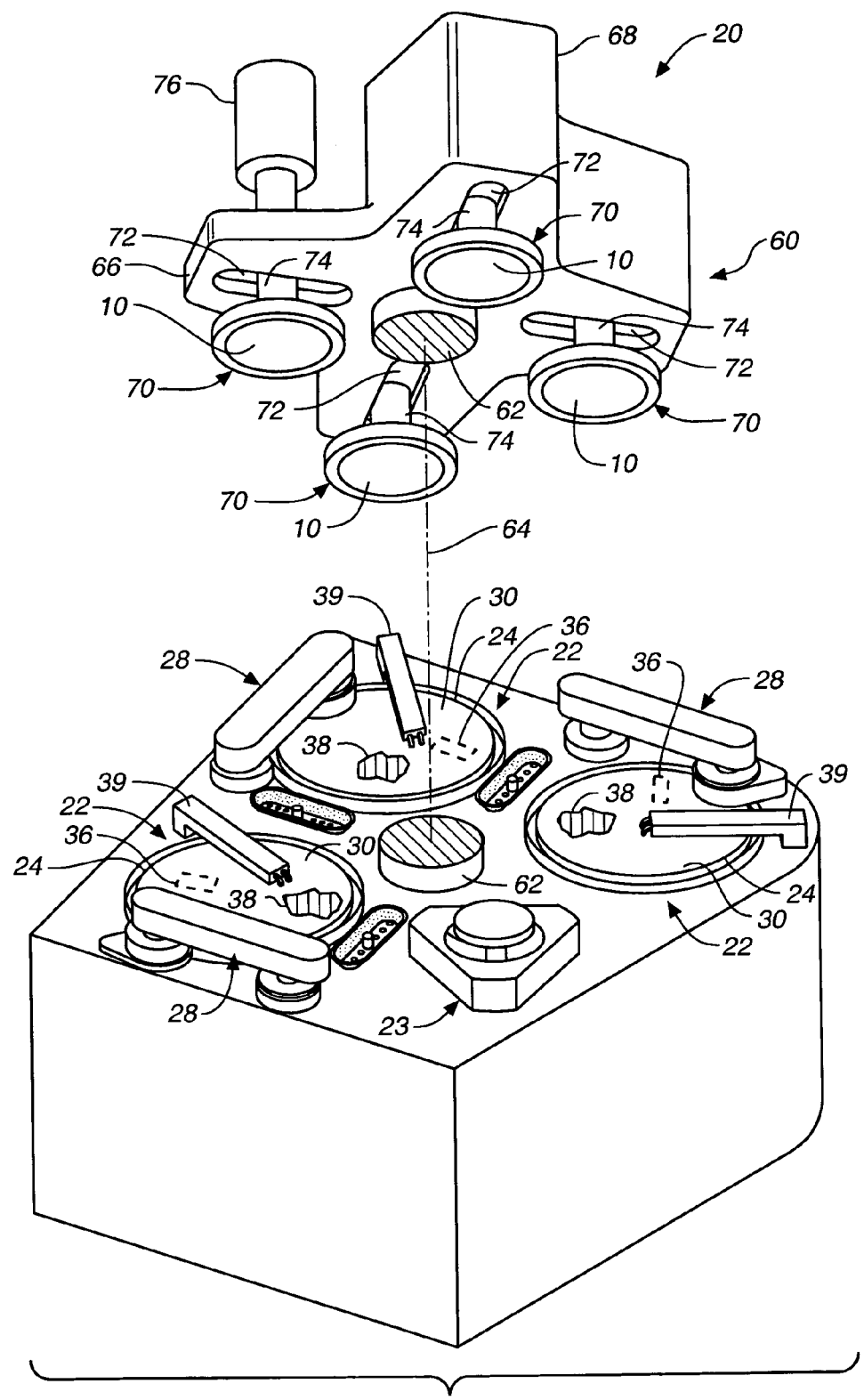
FIG._1

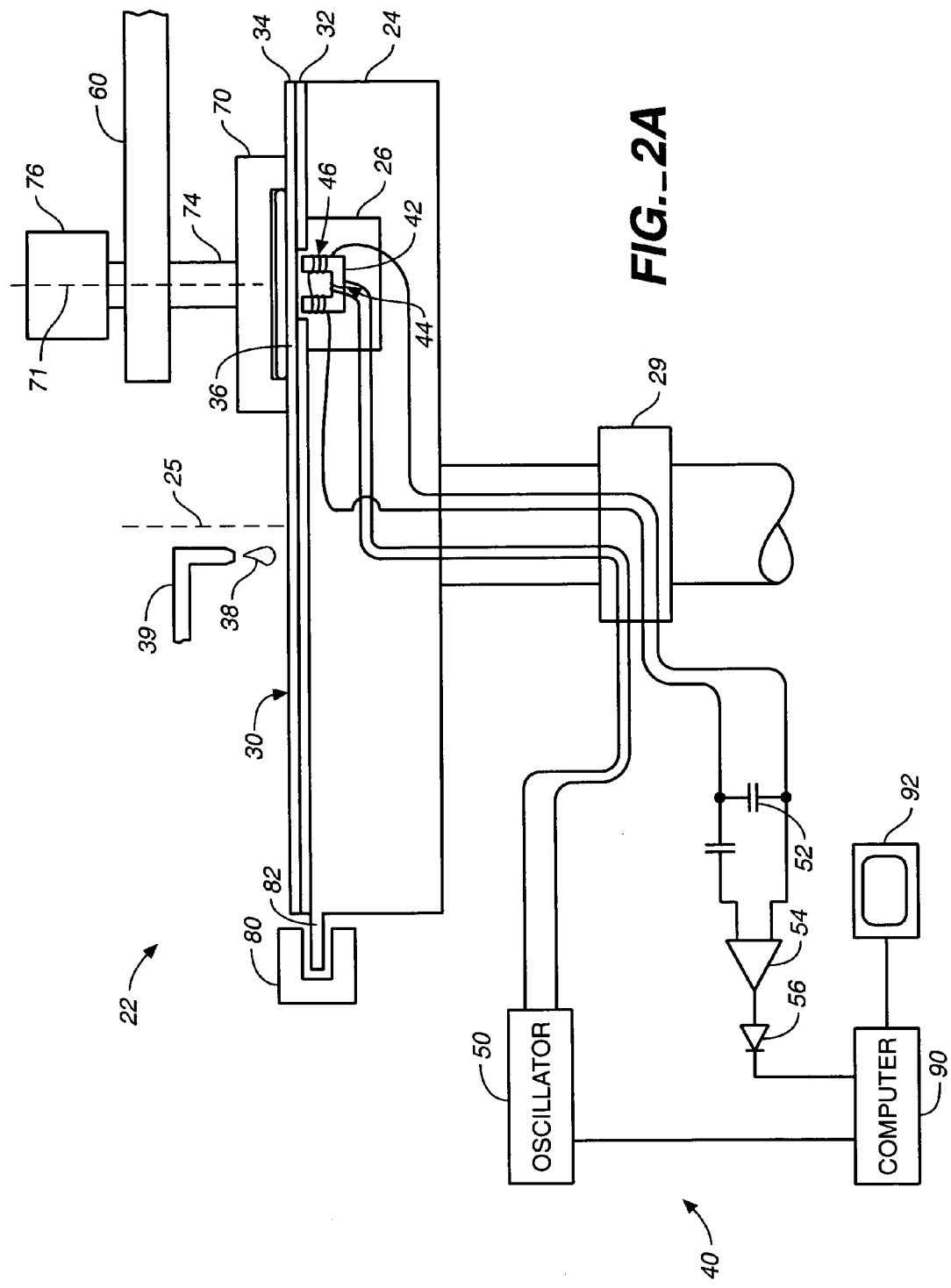
FIG._2A

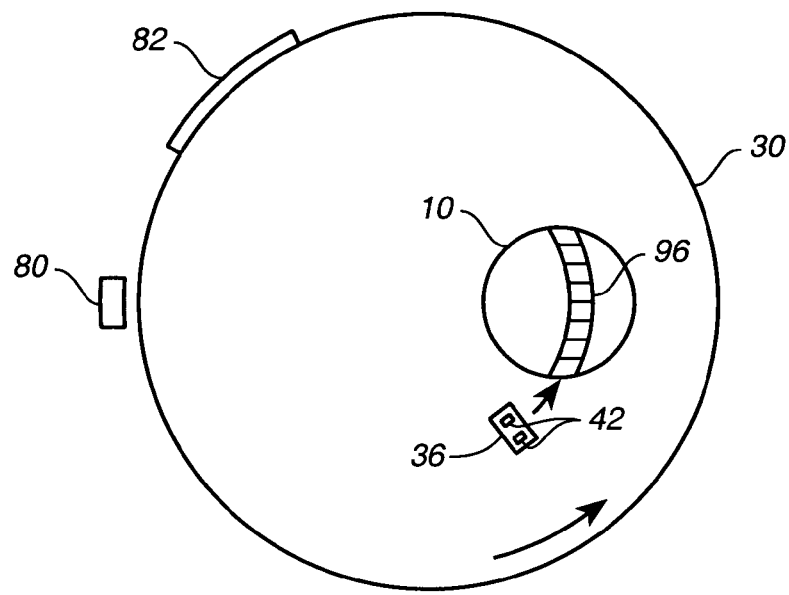
FIG._2B
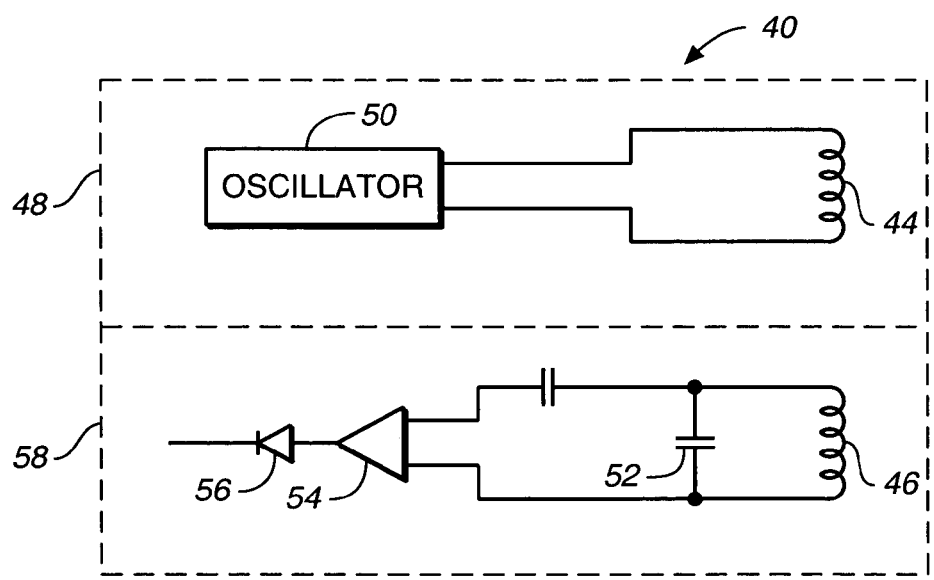
FIG._3

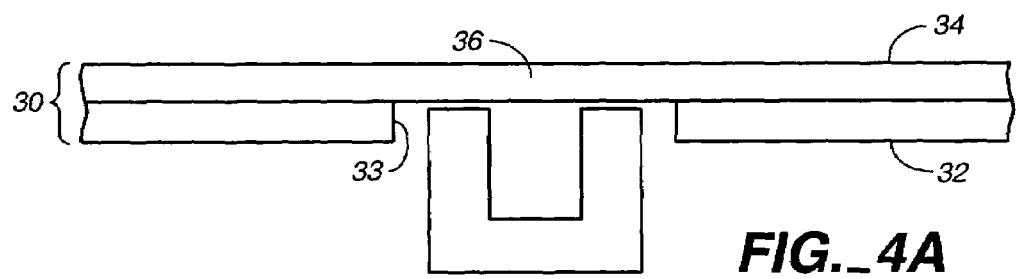
FIG._4A
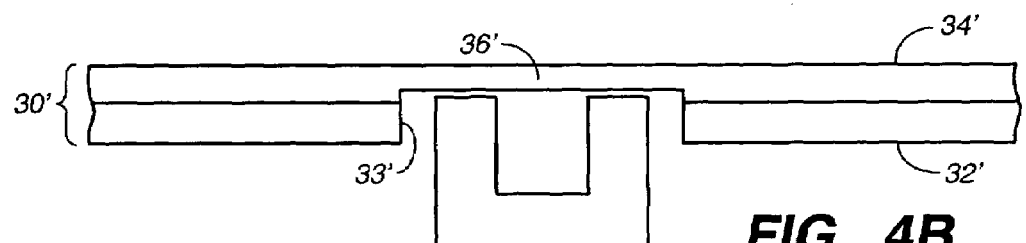
FIG._4B
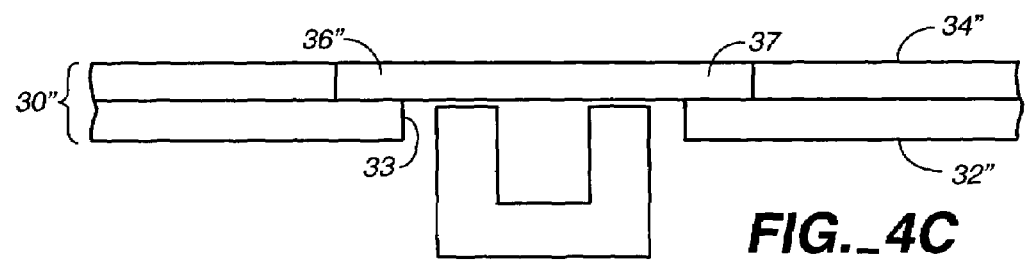
FIG._4C

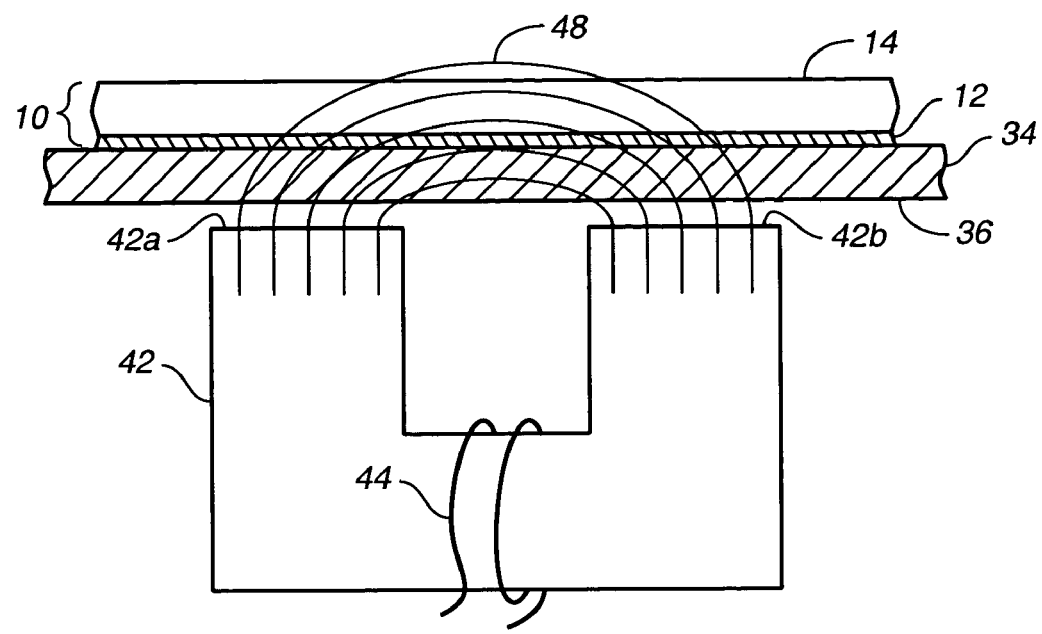
FIG._5
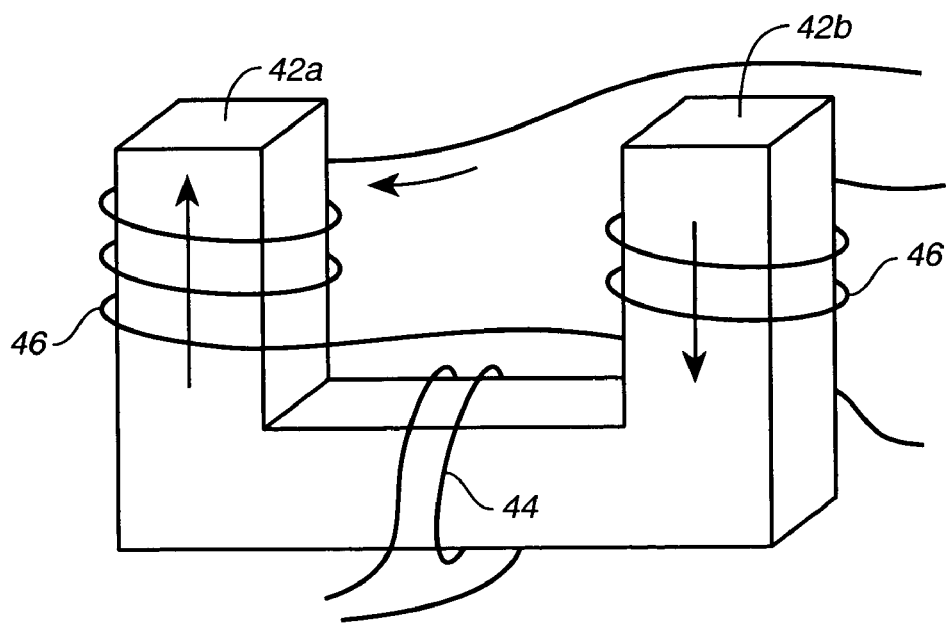
FIG._6

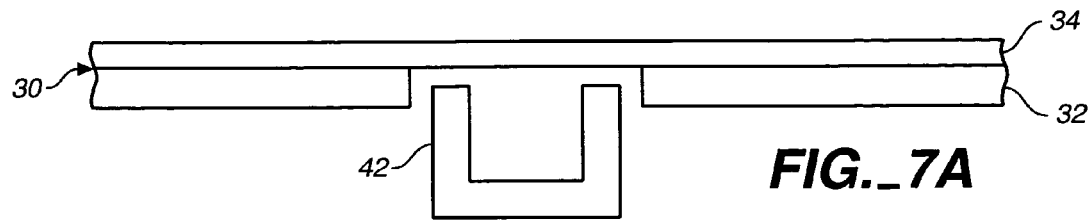
FIG._7A
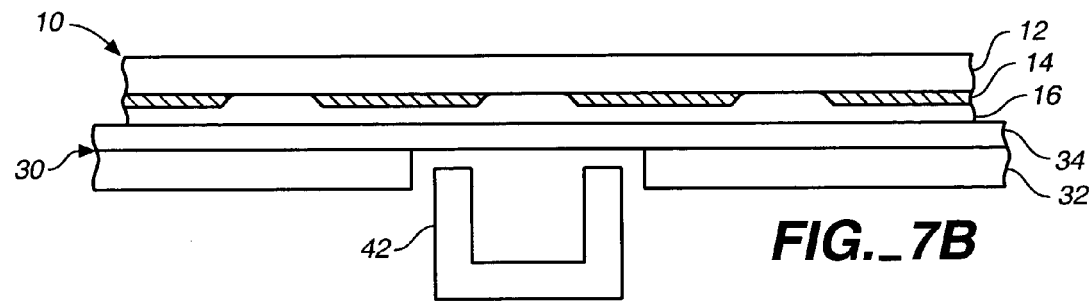
FIG._7B
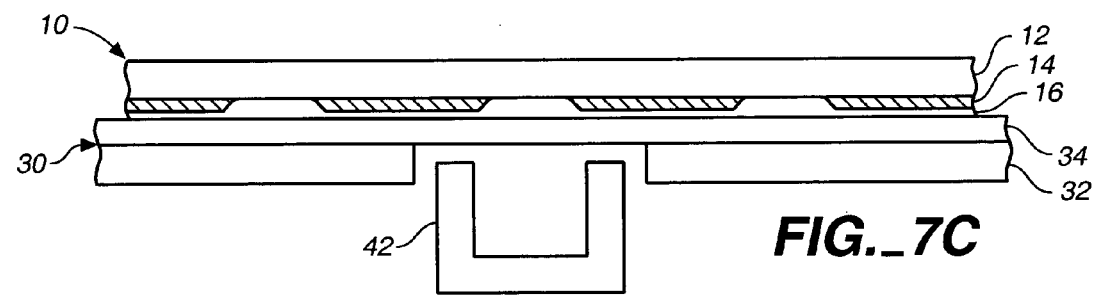
FIG._7C
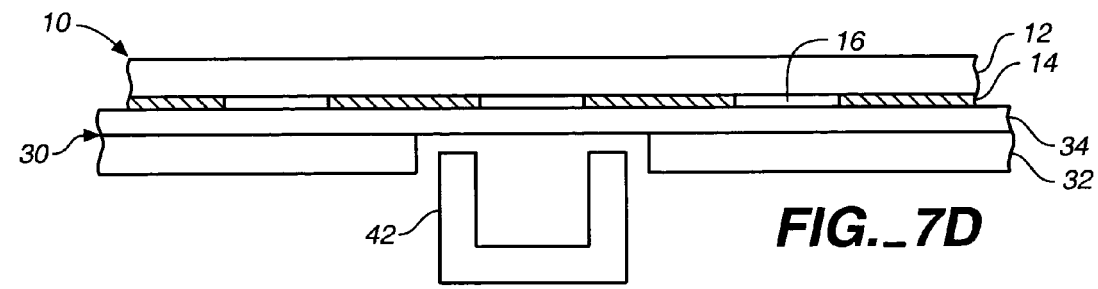
FIG._7D

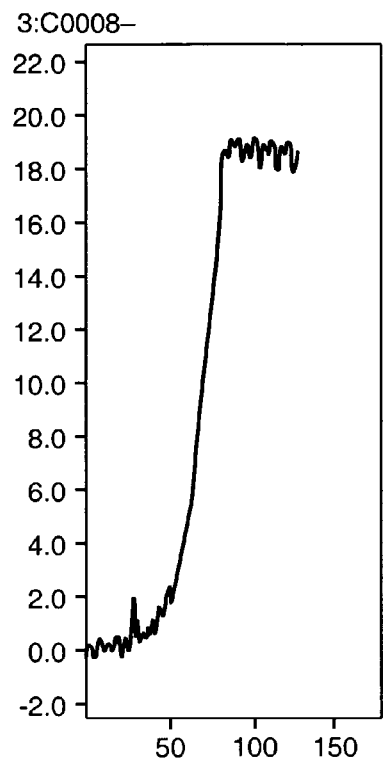
FIG._8
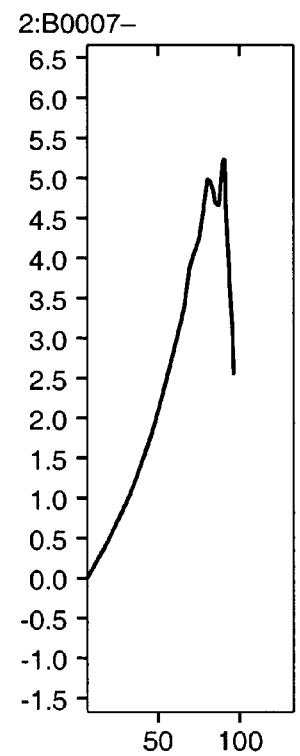
FIG._11
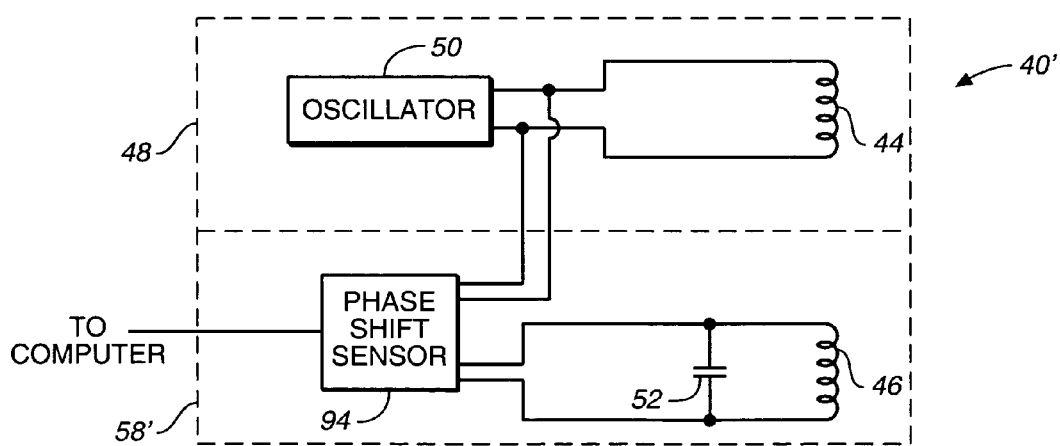
FIG._9

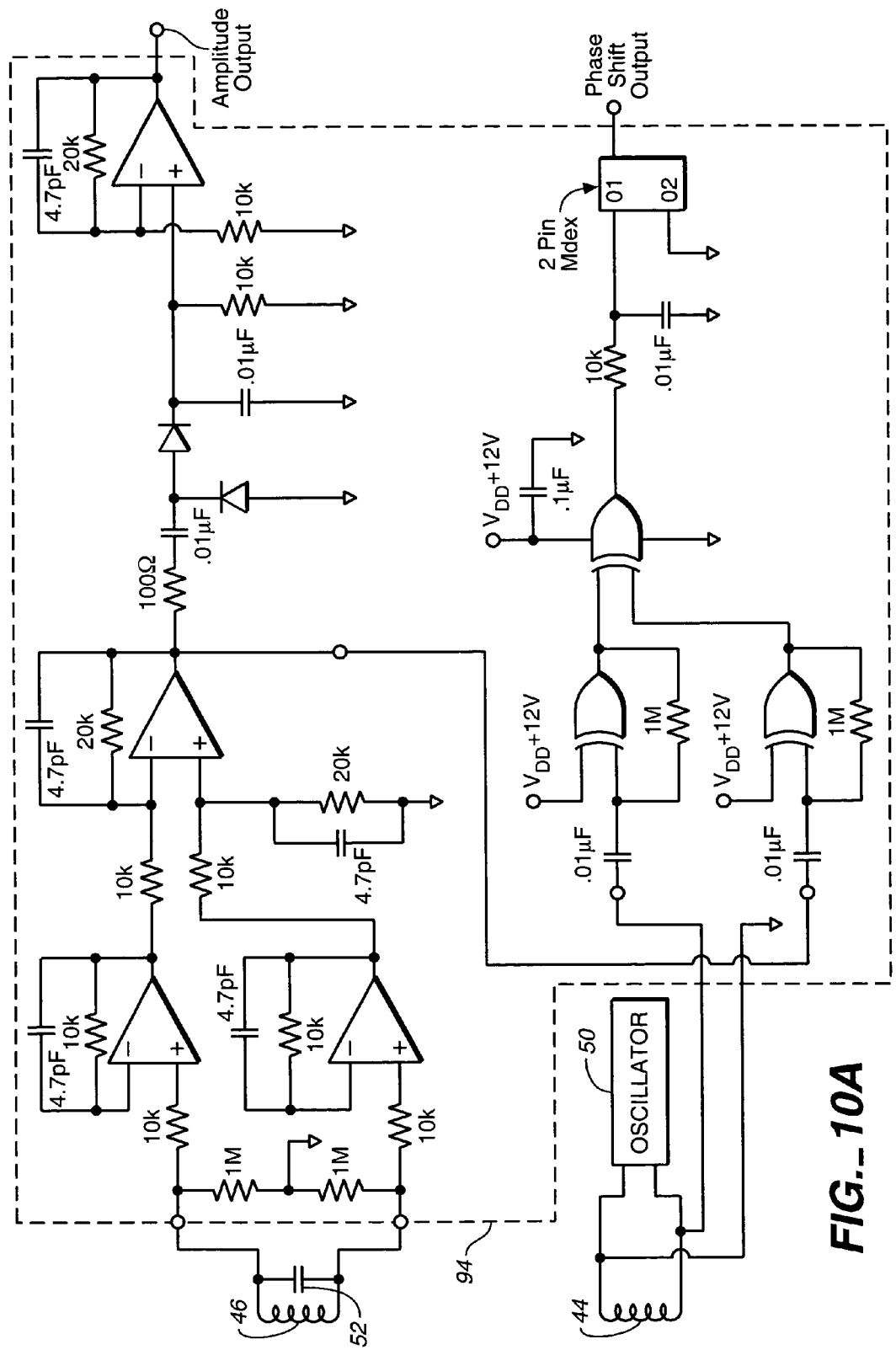
FIG._10A

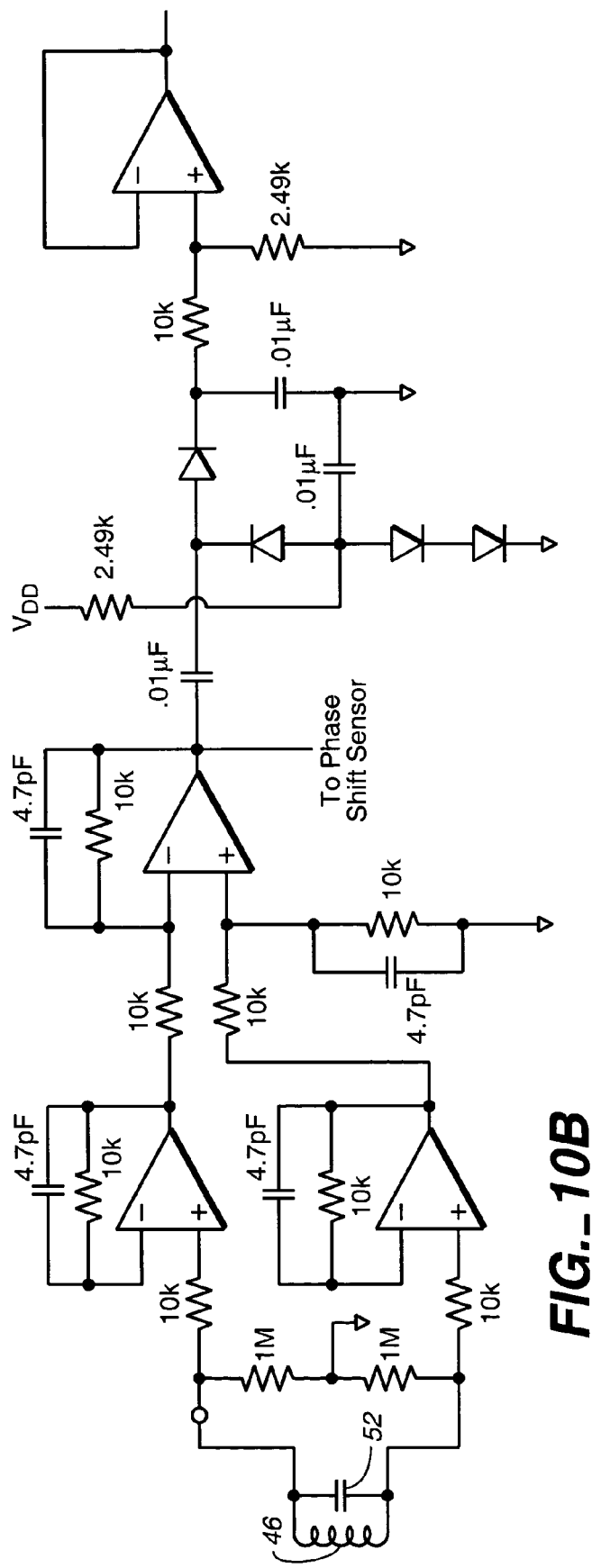
FIG._10B

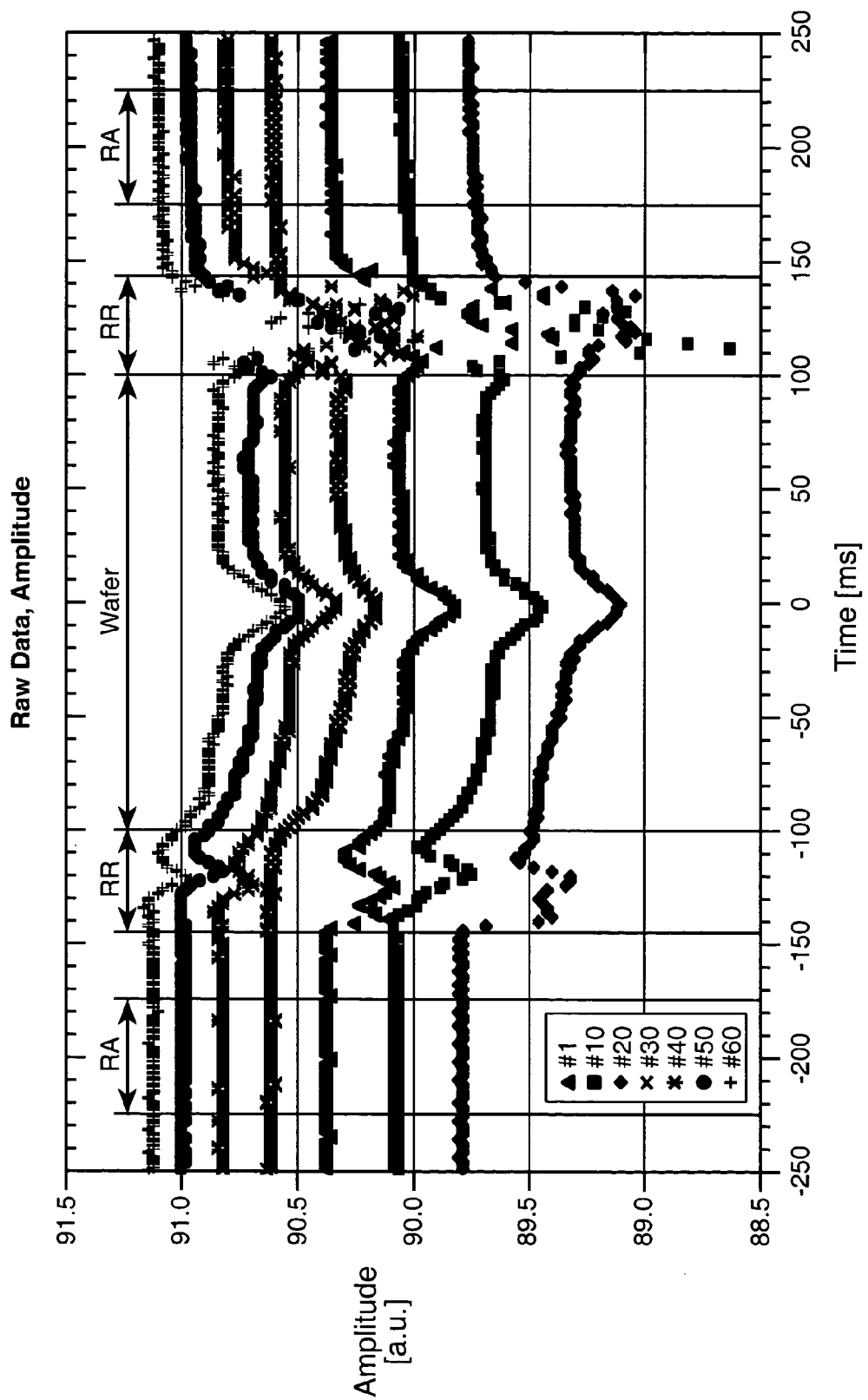
FIG._12

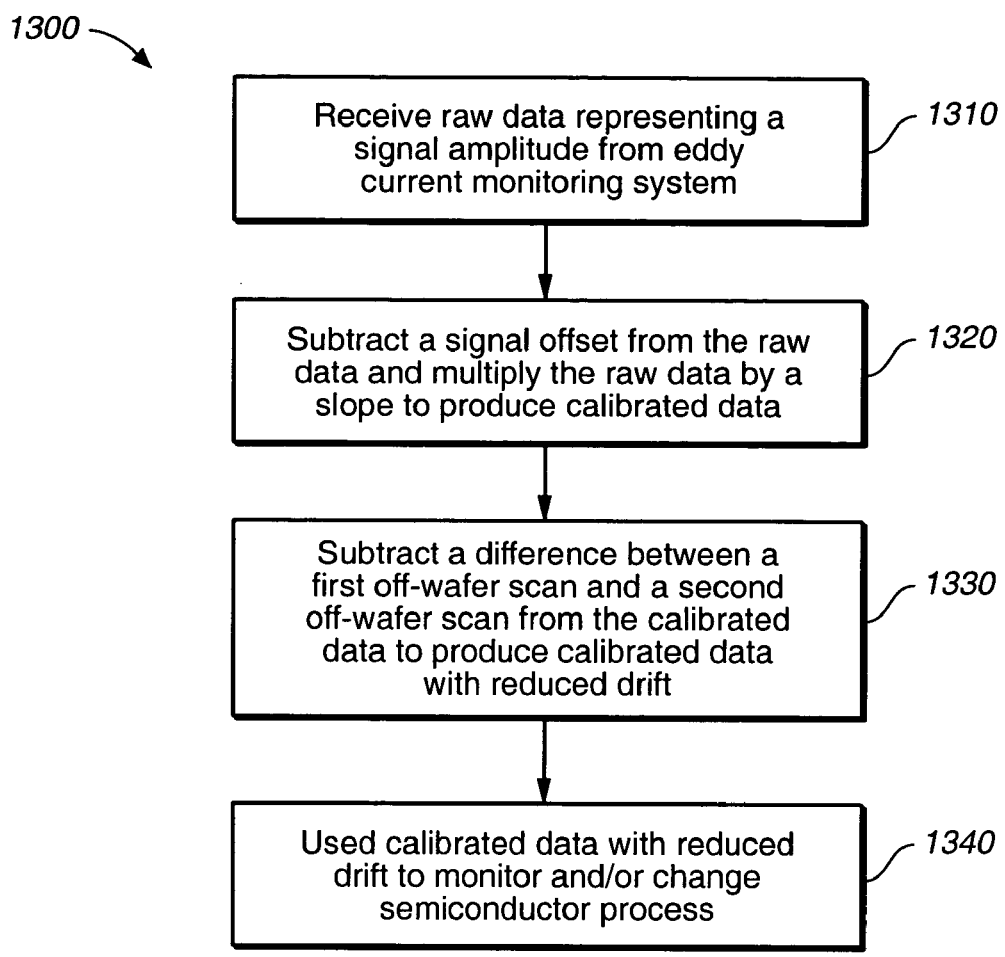
FIG._13

SIGNAL IMPROVEMENT IN EDDY CURRENT SENSING

BACKGROUND

This invention relates to semiconductor manufacturing, and more particularly to endpoint detection.

An integrated circuit is typically formed on a substrate by the sequential deposition of conductive, semiconductive or insulative layers on a silicon wafer. One fabrication step involves depositing a filler layer over a non-planar surface, and planarizing the filler layer until the non-planar surface is exposed. For example, a conductive filler layer can be deposited on a patterned insulative layer to fill the trenches or holes in the insulative layer. The filler layer is then polished until the raised pattern of the insulative layer is exposed. After planarization, the portions of the conductive layer remaining between the raised pattern of the insulative layer form vias, plugs and lines that provide conductive paths between thin film circuits on the substrate. In addition, planarization is needed to planarize the substrate surface for photolithography.

Chemical mechanical polishing (CMP) is one accepted method of planarization. This planarization method typically requires that the substrate be mounted on a carrier or polishing head. The exposed surface of the substrate is placed against a rotating polishing disk pad or belt pad. The polishing pad can be either a "standard" pad or a fixed-abrasive pad. A standard pad has a durable roughened surface, whereas a fixed-abrasive pad has abrasive particles held in a containment media. The carrier head provides a controllable load on the substrate to push it against the polishing pad. A polishing slurry, including at least one chemically-reactive agent, and abrasive particles if a standard pad is used, is supplied to the surface of the polishing pad.

One problem in CMP is determining whether the polishing process is complete, i.e., whether a substrate layer has been planarized to a desired flatness or thickness, or when a desired amount of material has been removed. Overpolishing (removing too much) of a conductive layer or film may lead to increased circuit resistance. On the other hand, underpolishing (removing too little) of a conductive layer may lead to electrical shorting. Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, the polishing endpoint cannot be determined merely as a function of polishing time.

One way to determine the polishing endpoint is to remove the substrate from the polishing surface and examine it. For example, the substrate can be transferred to a metrology station where the thickness of a substrate layer is measured, e.g., with a profilometer or a resistivity measurement. If the desired specifications are not met, the substrate is reloaded into the CMP apparatus for further processing. This is a time-consuming procedure that reduces the throughput of the CMP apparatus. Alternatively, the examination might reveal that an excessive amount of material has been removed, rendering the substrate unusable.

More recently, in-situ monitoring of the substrate has been performed, e.g., with optical or capacitance sensors, in order to detect the polishing endpoint. Other proposed endpoint detection techniques have involved measurements of friction, motor current, slurry chemistry, acoustics and conductivity. One detection technique that has been considered is to induce an eddy current in the metal layer and measure the change in the eddy current as the metal layer is removed.

The current disclosure provides methods and apparatus for providing accurate results both among different sensors and for a particular sensor during processing.

SUMMARY

A semiconductor processing apparatus may include an apparatus for measuring one or more properties of a conductive layer. For example, the apparatus may detect changing magnetic flux and produce a signal related to the changing magnetic flux. The signal related to the changing magnetic flux may be a measure of the thickness of a conductive layer on a semiconductor substrate.

According to an implementation, a method for semiconductor process may include detecting changing magnetic flux during semiconductor processing with a sensor and producing a signal based on the changing magnetic flux. The signal may be related to the amplitude of the changing magnetic flux, the phase of the changing magnetic flux, or a combination. The method may be used to determined properties of a conductive region on a semiconductor wafer. For example, the method may be used to determine the thickness of a conductive layer on a semiconductor layer, or to determine if an endpoint for a process related to a conductive layer has been reached.

The method may include processing the signal using one or more drift correction parameters. The drift correction parameters may include a first reference level. The first reference level may be set as a reference level obtained during sensor calibration, such as an off-wafer signal obtained during sensor calibration. The first reference level may be set as a reference level obtained during a reference scan, such as an off-wafer signal determined during a first or other scan. The first reference level may be determined using one or more data points. The one or more data points may be processed; for example, an average of an off-wafer signal in a particular off-wafer range may be used to determine the first reference level.

The drift correction parameters may include a second reference level. The second reference level may be set as a reference level obtained using off-wafer data obtained before and/or after the scan for which drift correction is being performed. For example, the second reference level may be determined using one or more data points. The one or more data points may include off-wafer data from prior to the scan and/or subsequent to the scan. The one or more data points may be processed; for example, by averaging. Data points from other scans may be used as well. For example, off-wafer data points from previous and/or subsequent scans may be used. In an implementation, off-wafer data points from one or more previous scans may be used to determine at least a slope of an off-wafer signal.

Drift correction may include determining a difference between first and second reference levels, a ratio between first and second reference levels, or a combination. Drift correction may additionally include a correction based on the approximate thickness of the conductive layer, or other parameter.

The method may further include processing the signal using one or more calibration parameters. The calibration parameters may include a slope and an offset. The calibration parameters may include a reference high, a reference low, a setpoint high, and/or a setpoint low. A reference high may be related to a signal obtained by the sensor when the sensor is not proximate to a conductive region with known properties. For example, the reference high may be related to a signal obtained by the sensor when the sensor is off-wafer, and the wafer includes a conductive layer of a known thickness of a particular conductor.

A reference low may be related to a signal obtained by the sensor when the sensor is proximate to a conductive region with known properties. For example, the reference low may be related to a signal obtained by the sensor when the sensor is on-wafer, and the wafer includes a conductive layer of a known thickness of a particular conductor.

A setpoint high may be chosen. For example, a setpoint high may be chosen as a typical reading for a signal obtained by the sensor when the sensor is not proximate to a conductive region with known properties, such as a conductive layer of a known thickness of a particular conductor on a semiconductor layer.

A setpoint low may be chosen. For example, a setpoint low may be chosen as a typical reading for a signal obtained by the sensor when the sensor is proximate to a conductive region with known properties, such as a conductive layer of a known thickness of a particular conductor on a semiconductor layer.

The details of one or more implementations are set forth in the accompanying drawings and the description below. Other features and advantages will be apparent from the description and drawings, and from the claims.

DESCRIPTION OF DRAWINGS

FIG. 1 is a schematic exploded perspective view of a chemical mechanical polishing apparatus.

FIG. 2A is a schematic side view, partially cross-sectional, of a chemical mechanical polishing apparatus including an eddy current monitoring system.

FIG. 2B is a schematic top view of a chemical mechanical polishing apparatus including an eddy current monitoring system, showing a path of a sensor scan across a wafer.

FIG. 3 is a schematic circuit diagram of the eddy current monitoring system.

FIGS. 4A–4C are schematic cross-sectional views of a polishing pad.

FIG. 5 is a schematic cross-sectional view illustrating a magnetic field generated by the monitoring system.

FIG. 6 is a schematic perspective view of a core from an eddy current sensor.

FIGS. 7A–7D schematically illustrating a method of detecting a polishing endpoint using an eddy current sensor.

FIG. 8 is a graph illustrating a trace from the eddy current monitoring system.

FIG. 9 is a schematic diagrams an eddy current monitoring system that senses a phase shift.

FIGS. 10A and 10B are schematic circuit diagrams of two implementations of an eddy current monitoring system of FIG. 9.

FIG. 11 is a graph illustrating a trace from the eddy current monitoring system that measures phase shift.

FIG. 12 is a plot illustrating drift in an amplitude signal measured with an eddy current monitoring system.

FIG. 13 is a flow diagram illustrating steps for processing eddy current data using one or more calibration parameters and one or more drift parameters.

Like reference symbols in the various drawings indicate like elements.

DETAILED DESCRIPTION

According to some implementations, a signal from an eddy current sensor or other sensor is processed so that the data is calibrated and so that signal drift may be reduced or eliminated.

Interpreting signals from eddy current sensors may be difficult due to a number of factors. Interpreting signals from a particular sensor may be difficult due to sensor-to-sensor differences, such as the way in which the coils are wound on the sensor core, slight differences in core dimensions or other dimensions, and batch-to-batch variations in core materials. For a particular sensor, a change in the distance between the sensor and the wafer has a strong impact on measured signals (the "lift-off effect"). Process conditions, such as a change in temperature of the sensor due to heat produced by polishing, may also have an impact on the eddy current signal. Finally, ambient conditions, such as the temperature and humidity may have an effect on the eddy current signal. One or more of these factors may lead to different signal strengths and/or phase values for a given conductive layer profile.

In an implementation, an eddy current sensor is provided in a chemical mechanical polishing apparatus such as a CMP apparatus 20 of FIGS. 1 and 2A. A description of a similar polishing apparatus 20 can be found in U.S. Pat. No. 5,738,574, the entire disclosure of which is incorporated herein by reference.

One or more substrates 10 can be polished by CMP apparatus 20. Polishing apparatus 20 includes a series of polishing stations 22 and a transfer station 23. Transfer station 23 transfers the substrates between the carrier heads and a loading apparatus.

Each polishing station includes a rotatable platen 24 on which is placed a polishing pad 30. The first and second stations can include a two-layer polishing pad with a hard durable outer surface or a fixed-abrasive pad with embedded abrasive particles. The final polishing station can include a relatively soft pad. Each polishing station can also include a pad conditioner apparatus 28 to maintain the condition of the polishing pad so that it will effectively polish substrates.

A rotatable multi-head carousel 60 supports four carrier heads 70. The carousel is rotated by a central post 62 about a carousel axis 64 by a carousel motor assembly (not shown) to orbit the carrier head systems and the substrates attached thereto between polishing stations 22 and transfer station 23. Three of the carrier head systems receive and hold substrates, and polish them by pressing them against the polishing pads. Meanwhile, one of the carrier head systems receives a substrate from and delivers a substrate to transfer station 23.

Each carrier head 70 is connected by a carrier drive shaft 74 to a carrier head rotation motor 76 (shown by the removal of one quarter of cover 68) so that each carrier head can independently rotate about it own axis. In addition, each carrier head 70 independently laterally oscillates in a radial slot 72 formed in carousel support plate 66. A description of a suitable carrier head 70 can be found in U.S. Pat. No. 6,422,927, filed Dec. 23, 1999, issued Jul. 23, 2002, the entire disclosure of which is incorporated by reference. In operation, the platen is rotated about its central axis 25, and the carrier head is rotated about its central axis 71 and translated laterally across the surface of the polishing pad.

A slurry 38 containing a reactive agent (e.g., deionized water for oxide polishing) and a chemically-reactive catalyzer (e.g., potassium hydroxide for oxide polishing) can be supplied to the surface of polishing pad 30 by a slurry supply port or combined slurry/rinse arm 39. If polishing pad 30 is a standard pad, slurry 38 can also include abrasive particles (e.g., silicon dioxide for oxide polishing). Referring to FIGS. 2A and 3, a recess 26 is formed in platen 24, and a thin section 36 can be formed in polishing pad 30 overlying recess 26. Aperture 26 and thin pad section 36, if needed, are positioned such that they pass beneath substrate 10 during a portion of the platen's rotation, regardless of the translational position of the carrier head. Assuming that polishing pad 32 is a two-layer pad, thin pad section 36 can be constructed as shown in FIG. 4A by removing a portion 33 of backing layer 32. Alternatively, as shown in FIG. 4B, thin pad section 36' can be formed by removing a portion 33' of both backing layer 32' and a portion of cover layer 34'. Thus, this implementation has a recess in the bottom surface of cover layer 34 in the thin pad section 36. If the polishing pad is a single-layer pad, thin pad section 36 can be formed by removing a portion of the pad material to create a recess in the bottom surface of the pad. Alternatively, as shown in FIG. 4C, thin pad section 36" can be formed by inserting a plug 37 of a different material into polishing pad 30. For example, the plug can be a relatively pure polymer or polyurethane, e.g., formed without fillers. In general, the material of pad section 36 should be non-magnetic and non-conductive. If the polishing pad is itself sufficiently thin or has a magnet permeability (and conductivity) that does not interfere with the eddy current measurements, then the pad does not need any modifications or recesses.

Returning to FIGS. 2A and 3, an in-situ eddy current monitoring system 40, which can function as an endpoint detector, includes a drive system 48 to induce eddy currents in a metal layer on the substrate and a sensing system 58 to detect eddy currents induced in the metal layer by the drive system. The monitoring system 40 includes a core 42 positioned in recess 26 to rotate with the platen, a drive coil 44 wound around one part of core 42, and a sense coil 46 wound around second part of core 42. For drive system 48, monitoring system 40 includes an oscillator 50 connected to drive coil 44. For sense system 58, monitoring system 40 includes a capacitor 52 connected in parallel with sense coil 46, an RF amplifier 54 connected to sense coil 46, and a diode 56. The oscillator 50, capacitor 52, RF amplifier 54, and diode 56 can be located apart from platen 24, and can be coupled to the components in the platen through a rotary electrical union 29.

Referring to FIG. 5, in operation the oscillator 50 drives drive coil 44 to generate an oscillating magnetic field 48 that extends through the body of core 42 and into the gap 46 between the two poles 42a and 42b of the core. At least a portion of magnetic field 48 extends through thin portion 36 of polishing pad 30 and into substrate 10. If a metal layer 12 is present on substrate 10, oscillating magnetic field 48 generates eddy currents in the metal layer 12. The eddy currents cause the metal layer 12 to act as an impedance source in parallel with sense coil 46 and capacitor 52. As the thickness of the metal layer changes, the impedance changes, resulting in a change in the Q-factor of the sensing mechanism. By detecting the change in the Q-factor of the sensing mechanism, the eddy current sensor can sense the change in the strength of the eddy currents, and thus the change in thickness of metal layer 12.

Referring to FIG. 6, core 42 can be a U-shaped body formed of a non-conductive material with a relatively high magnetic permeability (e.g., $\mu$ of about 2500). Specifically, core 42 can be ferrite. In one implementation, the two poles 42a and 42b are about 0.6 inches apart, the core is about 0.6 inches deep, and the cross-section of the core is a square about 0.2 inches on a side.

In general, the in-situ eddy current monitoring system 40 is constructed with a resonant frequency of about 50 kHz to 10 MHz, e.g., 2 MHz. For example, the sense coil 46 can have an inductance of about 0.3 to 30 $\mu$H and the capacitor 52 can have a capacitance of about 0.2 to 20 nF. The driving coil can be designed to match the driving signal from the oscillator. For example, if the oscillator has a low voltage and a low impedance, the drive coil can include fewer turns to provide a small inductance. On the other hand, if the oscillator has a high voltage and a high impedance, the drive coil can include more turns to provide a large inductance.

In one implementation, the sense coil 46 includes nine turns around each prong of the core, and the drive coil 44 includes two turns around the base of the core, and the oscillator drives the drive coil 44 with an amplitude of about 0.1 V to 5.0 V. Also, in one implementation, the sense coil 46 has an inductance of about 2.8 $\mu$H, the capacitor 52 has a capacitance of about 2.2 nF, and the resonant frequency is about 2 MHz. In another implementation, the sense coil has an inductance of about 3 $\mu$H and the capacitor 52 has a capacitance of about 400 pF. Of course, these values are merely exemplary, as they are highly sensitive to the exact winding configuration, core composition and shape, and capacitor size.

In general, the greater the expected initial thickness of the conductive film, the lower the desired resonant frequency. For example, for a relatively thin film, e.g., 2000 Angstroms, the capacitance and inductance can be selected to provide a relatively high resonant frequency, e.g., about 2 MHz. On the other hand, for a relatively thicker film, e.g., 20000 Angstroms, the capacitance and inductance can be selected to provide a relatively lower resonant frequency, e.g., about 50 kHz. However, high resonant frequencies may still work well with thick copper layers. In addition, very high frequencies (above 2 MHz) can be used to reduce background noise from metal parts in the carrier head.

Returning to FIGS. 24, 2B and 3, the CMP apparatus 20 can also include a position sensor 80, such as an optical interrupter, to sense when COre 42 is beneath substrate 10. For example, the optical interrupter could be mounted at a fixed point opposite carrier head 70. A flag 82 is attached to the periphery of the platen. The point of attachment and length of flag 82 is selected so that it interrupts the optical signal of sensor 80 while core 42 sweeps beneath substrate 10. Alternatively, the CMP apparatus can include an encoder to determine the angular position of platen.

In operation, CMP apparatus 20 uses monitoring system 40 to determine when the bulk of the filler layer has been removed and the underlying stop layer has been exposed. Monitoring system 40 can as be used to determine the amount of material removed from the surface of the substrate. A general purpose programmable digital computer 90 can be connected to amplifier 56 to receive the intensity signal from the eddy current sensing system. Computer 90 can be programmed to sample amplitude measurements from the monitoring system when the substrate generally overlies the core, to store the amplitude measurements, and to apply the endpoint detection logic to the measured signals to detect the polishing endpoint. Possible endpoint criteria for the detector logic include local minima or maxima, changes in slope, threshold values in amplitude or slope, or combinations thereof.

Referring to FIG. 2B, the core 42, drive coil 44 and sense coil 46 of the eddy current sensor located below thin section 36 of polishing pad 32 sweep beneath the substrate with each rotation of the platen. Therefore, the computer 90 can also be programmed to divide the amplitude measurements from each sweep of the core beneath the substrate into a plurality of sampling zones 96, to calculate the radial position of each sampling zone, to sort the amplitude measurements into radial ranges, to determine minimum, maximum and average amplitude measurements for each sampling zone, and to use multiple radial ranges to determine the polishing endpoint, as discussed in U.S. Pat. No. 6,399,501, filed Dec. 13, 1999, issued Jun. 4, 2002, the entirety of which is incorporated herein by reference.

Since the eddy current sensor sweeps beneath the substrate with each rotation of the platen, information on the metal layer thickness is being accumulated in-situ and on a continuous real-time basis. In fact, the amplitude measurements from the eddy current sensor can be displayed on an output device 92 during polishing to permit the operator of the device to visually monitor the progress of the polishing operation.

Moreover, after sorting the amplitude measurements into radial ranges, information on the metal film thickness can be fed in real-time into a closed-loop controller to periodically or continuously modify the polishing pressure profile applied by a carrier head, as discussed in U.S. patent application Ser. No. 60/143,219, filed Jul. 7, 1999, the entirety of which is incorporated herein by reference. For example, the computer could determine that the endpoint criteria have been satisfied for the outer radial ranges but not for the inner radial ranges. This would indicate that the underlying layer has been exposed in an annular outer area but not in an inner area of the substrate. In this case, the computer could reduce the diameter of the area in which pressure is applied so that pressure is applied only to the inner area of the substrate, thereby reducing dishing and erosion on the outer area of the substrate. Alternatively, the computer can halt polishing of the substrate on the first indication that the underlying layer has been exposed anywhere on the substrate, i.e., at first clearing of the metal layer.

Initially, referring to FIGS. 2A, 3 and 7A, oscillator 50 is tuned to the resonant frequency of the LC circuit, without any substrate present. This resonant frequency results in the maximum amplitude of the output signal from RF amplifier 54.

As shown in FIGS. 7B and 8, for a polishing operation, a substrate 10 is placed in contact with polishing pad 30. Substrate 10 can include a silicon wafer 12 and a conductive layer 16, e.g., a metal such as copper, disposed over one or more patterned underlying layers 14, which can be semiconductor, conductor or insulator layers. The patterned underlying layers can include metal features, e.g., vias, pads and interconnects. Since, prior to polishing, the bulk of conductive layer 16 is initially relatively thick and continuous, it has a low resistivity, and relatively strong eddy currents can be generated in the conductive layer. As previously mentioned, the eddy currents cause the metal layer to function as an impedance source in parallel with sense coil 46 and capacitor 52. Consequently, the presence of conductive film 16 reduces the Q-factor of the sensor circuit, thereby significantly reducing the amplitude of the signal from RF amplifier 56.

Referring to FIGS. 7C and 8, as substrate 10 is polished, the bulk portion of conductive layer 16 is thinned. As the conductive layer 16 thins, its sheet resistivity increases, and the eddy currents in the metal layer become dampened. Consequently, the coupling between metal layer 16 and sensor circuitry 58 is reduced (i.e., increasing the resistivity of the virtual impedance source). As the coupling declines, the Q-factor of the sensor circuit 58 increases toward its original value.

Referring to FIGS. 7D and 8, eventually the bulk portion of conductive layer 16 is removed, leaving conductive interconnects 16' in the trenches between the patterned insulative layer 14. At this points, the coupling between the conductive portions in the substrate, which are generally small and generally non-continuous, and sensor circuit 58 reaches a minimum. Consequently, the Q-factor of the sensor circuit reaches a maximum value (although not as large as the Q-factor when the substrate is entirely absent). This causes the amplitude of the output signal from the sensor circuit to plateau. Thus, by sensing when the amplitude of the output signal is no longer increasing and has leveled off (e.g., reached a local plateau), computer 90 can sense a polishing endpoint. Alternatively, by polishing one or more test substrates, the operator of the polishing machine can determine the amplitude of the output signal as a function of the thickness of the metal layer. Thus, the endpoint detector can halt polishing when a particular thickness of the metal layer remains on the substrate. Specifically, computer 90 can trigger the endpoint when the output signal from the amplifier exceeds a voltage threshold corresponding to the desired thickness.

The eddy current monitoring system can also be used to trigger a change in polishing parameters. For example, when the monitoring system detects a polishing criterion, the CMP apparatus can change the slurry composition (e.g., from a high-selectivity slurry to a low selectivity slurry). As another example, as discussed above, the CMP apparatus can change the pressure profile applied by the carrier head.

In addition to sensing changes in amplitude, the eddy current monitoring system can calculate a phase shift in the sensed signal. As the metal layer is polished, the phase of the sensed signal changes relative to the drive signal from the oscillator 50. This phase difference can be correlated to the thickness of the polished layer. One implementation of a phase measuring device, shown in FIG. 1A, combines the drive and sense signals to generate a phase shift signal with a pulse width or duty cycle which is proportional to the phase difference. In this implementation, two XOR gates 100 and 102 are used to convert sinusoidal signals from the sense coil 46 and oscillator 50, respectively, into square-wave signals. The two square-wave signals are fed into the inputs of a third XOR gate 104. The output of the third XOR gate 104 is a phase shift signal with a pulse width or duty cycle proportional to the phase difference between the two square wave signals. The phase shift signal is filtered by an RC filter 106 to generate a DC-like signal with a voltage proportional to the phase difference. Alternatively, the signals can be fed into a programmable digital logic, e.g., a Complex Programmable Logic Device (CPLD) or Field Programmable Gate Array (FGPA) that performs the phase shift measurements.

The phase shift measurement can be used to detect the polishing endpoint in the same fashion as the amplitude measurements discussed above. Alternatively, both amplitude and phase shift measurements could be used in the endpoint detection algorithm. An implementation for both the amplitude and phase shift portions of the eddy current monitoring system is shown in FIG. 10A. An implementation of the amplitude sensing portion of the eddy current monitoring system is shown in FIG. 10B. An example of a trace generated by an eddy current monitoring system that measures the phase difference between the drive and sense signals is shown in FIG. 11. Since the phase measurements are highly sensitive to the stability of the driving frequency, phase locked loop electronics may be added.

A possible advantage of the phase difference measurement is that the dependence of the phase difference on the metal layer thickness may be more linear than that of the amplitude. In addition, the absolute thickness of the metal layer may be determined over a wide range of possible thicknesses.

The eddy current monitoring system can be used in a variety of polishing systems. Either the polishing pad, or the carrier head, or both can move to provide relative motion between the polishing surface and the substrate. The polishing pad can be a circular (or some other shape) pad secured to the platen, a tape extending between supply and take-up rollers, or a continuous belt. The polishing pad can be affixed on a platen, incrementally advanced over a platen between polishing operations, or driven continuously over the platen during polishing. The pad can be secured to the platen during polishing, or there could be a fluid bearing between the platen and polishing pad during polishing. The polishing pad can be a standard (e.g., polyurethane with or without fillers) rough pad, a soft pad, or a fixed-abrasive pad. Rather than tuning when the substrate is absent, the drive frequency of the oscillator can be tuned to a resonant frequency with a polished or unpolished substrate present (with or without the carrier head), or to some other reference.

A chemical mechanical polishing apparatus such as CMP apparatus 20 of FIG. 1 above with an in-situ eddy current monitoring system such as system 40 of FIGS. 2A and 3 can be used to detect induced eddy currents in a conductive layer in order to, for example, measure the thickness of the conductive layer. However, a number of factors may prevent accurate determination of the thickness of a conductive layer (or alternatively, whether a desired endpoint in a process has been reached). First, differences among different sensors and their positioning within a chemical mechanical polishing apparatus may lead to different results. Second, differences in the measurements obtained by a particular sensor at different times and processing conditions—i.e., sensor drift—may lead to inaccurate results. Sensor drift maybe caused by a number of factors, including changes in temperature. For example, during a chemical mechanical polishing process, significant heat may be generated as the shiny polishes the wafer. The heat may cause an increase in the temperature of various components of the eddy current measuring system and polishing system. The temperature increase may lead to a change in the measured signal.

In order to provide an accurate determination of the thickness of a conducting layer on the substrate, two things may be done. First, a particular sensor may be calibrated with other sensors, so that the results may be interpreted reliably across sensors. Second, measurements taken with a particular sensor may be adjusted to compensate for drift.

In an implementation, a calibration process allows data from different sensors to be analyzed to obtain reliable results across different sensors. As stated above, each sensor may have slightly different characteristics, due to differences in fabricating the sensor itself and differences in mounting the sensor on the chemical mechanical polishing apparatus. E.g., differences in fabrication and/or mounting the sensor may result in different distances between the sensor and a conductive layer on a wafer, thus significantly affecting the signal. Differences may be caused by mismatch of the LC properties among different sensors. The core material, wire winding, precise sensor positioning and capacitance all influence the resonant frequency and loss of the entire sensor assembly.

In some implementations, a sensor may be calibrated a single time. In other implementations, a sensor may be calibrated more than once. For example, a sensor may be calibrated when initially installed on a chemical mechanical polishing apparatus. The sensor may be calibrated at additional times, such as during periodic maintenance, or after one or more particular actions have been taken (e.g., the sensor may be calibrated after any action in which the sensor was removed from the chemical mechanical polishing apparatus).

Different implementations of eddy current sensing methods may use different aspects of signals obtained from induced eddy currents. For example, phase information, amplitude information, or both may be used. Thus, a sensor may be calibrated for amplitude-related data, phase-related data, or both.

In one implementation, an algorithm for determining a thickness of a conductive layer on a substrate and/or for determining if a desired endpoint has been reached in a semiconductor processing step includes a number of parameters that may be set and/or determined to calibrate a sensor. For example, four parameters may be used to calibrate the sensor. A "setpoint high" may be chosen, representing the desired signal reading when a bare wafer is proximate to the sensor. The value for "setpoint high" may be chosen as a typical sensor reading for a sensor proximate to a bare wafer. Alternatively, "setpoint high" may correspond to a typical sensor reading when the sensor is "off wafer;" that is, when a wafer, which may or may not include a conductive layer, is in the chemical mechanical polishing system but is not proximate to the sensor.

Similarly, a "setpoint low" may be chosen, representing the desired signal reading when a wafer with a known thickness of a known conductor is present on a wafer proximate to the sensor. For example, the "setpoint low" may represent a typical reading for a sensor proximate to a wafer including a 20,000 Angstrom thick copper layer. The particular thickness chosen may be greater than the thickness typically measured by the sensor, so that in operation, data will be between the "setpoint low" and "setpoint high."

A "reference low" and "reference high" may then be measured using the sensor being calibrated. In order to measure the "reference high," a bare wafer may be placed in the chemical mechanical polishing system with the sensor. Alternatively, "reference high" may be measured when the sensor is off-wafer; that is, it is not proximate to a wafer, where the wafer may or may not include a conductive layer. In order to measure the "reference low," a wafer with the known thickness of the known conductor is placed in the chemical mechanical polishing system proximate to the sensor.

In some implementations, a single reading of each is made. In other implementations, more readings may be made. For example, reference high and reference low may be determined by placing a wafer with the known thickness of the known conductor in the chemical mechanical polishing system. The signal is measured one or more times when the wafer is proximate to the sensor ("on-wafer") and one or more times when the wafer is not proximate to the sensor ("off-wafer"). Reference low may be determined from the on-wafer readings (e.g., may be an average), while reference high may be determined from the off-wafer readings (e.g., may be an average).

Once the parameters have been determined and/or set, they may be entered into a configuration file for the particular sensor or stored in another manner for use with a sensing algorithm during processing. The sensing algorithm may then process the signal data during wafer processing using the calibration parameters.

For example, when the four calibration parameters outlined above are used, raw data may be adjusted using Equation (1) below, where $D_P$ represents data that has been processed using the calibration parameters, $D_R$ represents raw data obtained with the sensor, $R_L$ represents the reference low, $R_H$ represents the reference high, $S_H$ represents the setpoint high, and $S_L$ represents the setpoint low:

$$D_P = \left[(D_R - R_L) \cdot \frac{(S_H - S_L)}{(R_H - R_L)}\right] + S_L \quad \text{Equation (1)}$$

Although four parameters are set and/or determined in the example above and entered in a configuration file, a sensing algorithm may use fewer parameters. For example, Equation (1) can be rewritten as Equation (1a) below:

$$D_P = mD_R + b \quad \text{Equation (1a)}$$

In other words, the processed signal can be related to the raw signal by a slope, m, and an offset, b, where the slope is $\frac{(S_H - S_L)}{(R_H - R_L)}$ and the offset is $S_L - R_L \frac{(S_H - S_L)}{(R_H - R_L)}$.

The calibration process used above may be used with a drift compensation process. As stated above, as a particular sensor is used during polishing or other semiconductor process, the received signal may drift due to one or more factors. For example, as the system heats up during polishing, the size and/or position of the wafer, elements of the eddy current sensing system, and components of the chemical mechanical polishing system may change, which may cause the received signal to drift up or down. Further, the core's permeability and loss generally depend on temperature, and thus the core's magnetic properties are another source of temperature-dependent drift. In order to accurately determine a thickness of a conductive layer, or to determine whether an endpoint or other point in a semiconductor process has been reached, a method for drift compensation may be used.

Using a polishing system as described above with an eddy current sensor as described above, an amplitude signal such as that shown in FIG. 12 may be obtained.

FIG. 12 shows a number of scans across a wafer including a conductive layer. In regions marked as RA in FIG. 12, the sensor is not proximate to the wafer (the sensor is "off-wafer"). In regions marked as RR on FIG. 12, the sensor is proximate to a conductive retaining ring, which lowers the amplitude of the signal. In the region marked "Wafer" on FIG. 12, the sensor is proximate to the wafer (the sensor is "on-wafer").

As a conductive layer on the substrate is being polished, the on-wafer signal changes due to the changing thickness of the conductive layer. As the polishing progresses, material is removed from the conductive layer, and thus the resistance of the layer is increased. Thus, the on-wafer signal decreases as the polishing progresses. This decrease represents the actual change in thickness of the conductive layer.

However, the signal may change for other reasons as well. As mentioned above, as polishing progresses, the temperature of the wafer typically increases. The time-dependent increase in temperature may cause the signal to change over time. Other factors may contribute to signal drift as well.

In one implementation, in order to remove drift from an eddy current measurement, a change in a signal received when the sensor is not proximate to the conductive layer whose thickness is being measured (for example, an off-wafer signal) is used to estimate the amount of the on-wafer signal that is due to drift rather than a change in thickness of a conductive layer.

In one implementation, drift such as the drift illustrated in FIG. 12 is significantly reduced by applying Equation (2) below to the data, where $S_P(n)$ represents the processed signal for scan number n, $S_R(n)$ represents the raw signal for scan n, R(0) represents a first reference level, such an off-wafer or other reference signal for the first scan or an average off-wafer amplitude or phase as determined during sensor calibration. R(n) represents a second reference level; for example, an off-wafer signal for scan number n:

$$S_P(n) = S_R(n) \cdot \frac{R(0)}{R(n)} \quad \text{Equation (2)}$$

There are a number of ways in which R(n) may be determined. For example, when the reference signal is based on an off-wafer measurement with the sensor, the reference may be determined by averaging the off-wafer signal prior to scanning the wafer, by averaging the off-wafer signal subsequent to scanning the wafer, by averaging the off-wafer signal from prior to and subsequent to scanning the wafer, by performing an average using a particular portion of the off-wafer signal, or by using particular values of the off-wafer signal. R(n) may include information from previous scans; for example, information based on data obtained during scans (n−1), (n−2), etc. For some implementations, R(n) may include information from subsequent scans; for example, information based on data obtained during scans (n+1), (n+2), etc. For example, when the thickness of a layer at a time prior to the endpoint of a process is of interest, information obtained subsequent to the scan performed at that time may be used to more accurately determine the thickness.

In other implementations of a process for reducing signal drift, a difference may be used rather than a ratio. In a simple example, the change in the reference signal (e.g., the off-wafer signal) is assumed to be due to drift, and that the drift in the desired signal can be approximated by the drift in the reference signal. The drift in the reference signal is then subtracted from the raw signal to yield a processed signal. For example, Formula (3) below may be used to correct for signal drift, where the variables in Formula (3) are denoted by the same symbols used in Formula (2) above:

$$S_P(n) = S_R(n) - [R(n) - R(0)] \quad \text{Equation (3)}$$

In other implementations, more complicated relationships may be used to compensate for drift. For example, signal drift may depend on the layer thickness or other parameter. That is, the ratio or difference used above may not accurately model the drift in conductive layers of different thicknesses. In such cases, one or more additional terms related to the thickness or other parameter may be used. Further, more complicated expressions utilizing both a ratio and a difference may be used to more accurately model drift. However, there may be simple cases where either a ratio such as that shown in Equation (2) or a difference as shown in Equation (3) may be used to model signal drift.

FIG. 13 shows a process 1300 that may be used to process amplitude data obtained from an eddy current monitoring system. Raw data is received from eddy current monitoring system (1310). A signal offset is subtracted from the raw data, which is then multiplied by a slope to produce calibrated data (1320). A difference between a first off-wafer scan and a second off-wafer scan is then subtracted from the calibrated data to produce calibrated data with reduced drift (1330). The calibrated data with reduced drift may then be used to monitor and/or change the semiconductor process (1340).

This process may be adapted to the different implementations such as those described above. For example, different calibration parameters may be used, and the data processed differently to obtain calibrated data. Different methods of compensating for drift may be used as well. Additionally, a phase signal may be processed rather than or in addition to an amplitude signal.

A number of embodiments of the invention have been described. Nevertheless, it will be understood that various modifications may be made without departing from the spirit and scope of the invention. For example, more or fewer calibration parameters may be used. Additionally, calibration and/or drift compensation methods may be altered. Accordingly, other embodiments are within the scope of the following claims.

What is claimed is:

1. An article comprising a machine-readable medium storing instructions operable to cause one or more machines to perform operations comprising:
   commencing a polishing step during which a conductive film on a substrate is polished by a semiconductor processing apparatus that includes an eddy current sensor;
   receiving a first portion of a signal, the first portion being generated by the eddy current sensor during the polishing step when the eddy current sensor is on-wafer, the first portion including a change in values represented by the signal;
   receiving a second portion of the signal, the second portion being generated by the eddy current sensor during the polishing step when the eddy current sensor is off-wafer;
   during the polishing step, comparing the second portion of the signal to a reference signal and determining, based on a result of the comparing, a value for a drift correction parameter; and
   adjusting the first portion of the signal based on the drift correction parameter.

2. The article of claim 1, wherein:
   the signal includes portions from multiple scans of the eddy current sensor across the substrate, and the first and second portions are obtained from a first scan of the substrate, one scan of the substrate corresponding to one sweep of the eddy current sensor by the substrate.

3. The article of claim 2, wherein:
   the reference signal is a portion of the signal obtained during the polishing step when the eddy current sensor was off-wafer and before the first scan was effected.

4. The article of claim 3, wherein:
   the substrate processing apparatus includes a chemical mechanical polisher that includes a polishing pad situated on a platen, and polishing is effected by holding the substrate so that the film is in contact with the polishing pad as the platen rotates the polishing pad; and
   the eddy current sensor is situated in and rotates with the platen, the eddy current sensor sweeping by the substrate once per rotation of the platen.

5. The article of claim 3, wherein:
   a reference level is obtained from the reference signal and a first level is obtained from the second portion of the signal;
   the comparing is performed by taking a difference of the reference level and the first level; and
   the article further comprising instructions operable to process the signal by subtracting the difference from the signal, wherein the signal is adjusted to account for drift that occurred during the polishing step and in the eddy current sensor.

6. The article of claim 3, wherein:
   a reference level is obtained from the reference signal and a first level is obtained from the second portion of the signal;
   the comparing is performed by taking a ratio of the reference level and the first level; and
   the article further comprising instructions to process the signal by multiplying the signal with the ratio, wherein the signal is adjusted to account for drift tat occurred during the polishing step and in the eddy current sensor.

7. The article of claim 6, further comprising instructions operable to cause one or more machines to perform operations comprising:
   calibrating the eddy current sensor.

8. The article of claim 7, wherein calibrating includes:
   obtaining a setpoint high value that represents a target value for the signal from the eddy current sensor when the eddy current is off-wafer or when the substrate is a bare substrate;
   obtaining a setpoint low value that represents a target value for the signal from the eddy current sensor when the film on the substrate has a particular thickness;
   using the eddy current sensor to obtain a reference high value from the signal, which is measured when the eddy sensor current is off-wafer or when the substrate is a bare substrate;
   using the eddy current sensor to obtain a reference low value from the signal, which is measured when the substrate has the particular thickness; and
   processing the values to effect calibration.

9. The article of claim 8, wherein processing includes:
   calculating a slope as a ratio of a fist difference and a second difference, the first difference being between the setpoint high value and the setpoint low value and the second difference being between the reference high value and the reference low value; and
   calculating an offset as the setpoint low value.

10. The article of claim 9, wherein processing further includes:
    applying the slope and the offset to the signal.

11. The article of claim 1, wherein:
    the signal is a phase signal or an amplitude signal.

12. A computer-implemented method, comprising:
    commencing a polishing step during which a conductive film on a substrate is polished by a semiconductor processing apparatus that includes an eddy current sensor;
    receiving a first portion of a signal, the first portion being generated by the eddy current sensor during the polishing step when the eddy current sensor is on-wafer, the first portion including a change in values represented by the signal;

receiving a second portion of the signal, the second portion being generated by the eddy current sensor during the polishing step when the eddy current sensor is off-wafer;

during the polishing step, comparing the second portion of the signal to a reference signal and determining, based on a result of the comparing, a value for a drift correction parameter, and adjusting the first portion of the signal based on the drift correction parameter.

13. The method of claim 12, wherein:
the signal includes portions from multiple scans of the eddy current sensor across the substrate, and the first and second portions are obtained from a first scan of the substrate, one scan of the substrate corresponding to one sweep of the eddy current sensor by the substrate.

14. The method of claim 13, wherein:
the reference signal is a portion of the signal obtained during the polishing step when the eddy current sensor was off-wafer and before the first scan was effected.

15. The method of claim 14, wherein:
the substrate processing apparatus includes a chemical mechanical polisher that includes a polishing pad situated on a platen, and polishing is effected by holding the substrate so that the film is in contact with the polishing pad as the platen rotates the polishing pad; and the eddy current sensor is situated in and rotates with the platen, the eddy current sensor sweeping by the substrate once per rotation of the platen.

16. The method of claim 14, wherein:
a reference level is obtained from the reference signal and a first level is obtained from the second portion of the signal;

the comparing is performed by taking a ratio of the reference level and the first level; and the article further comprising instructions to process the signal by multiplying the signal with the ratio, wherein the signal is adjusted to account for drift that occurred during the polishing step and in the eddy current sensor.

17. The method of claim 14, wherein:
a reference level is obtained from the reference signal and a first level is obtained from the second portion of the signal;

the comparing is performed by taking a difference of the reference level and the first level; and the article further comprising instructions operable to process the signal by subtracting the difference from the signal, wherein the signal is adjusted to account for drift that occurred during the polishing step and in the eddy current sensor.

18. The method of claim 17, further comprising:
calibrating the eddy current sensor.

19. The method of claim 18, wherein calibrating includes:
obtaining a setpoint high value that represents a target value for the signal from the eddy current sensor when the eddy current is off-wafer or when the substrate is a bare substrate;

obtaining a setpoint low value that represents a target value for the signal from the eddy current sensor when the film on the substrate has a particular thickness;

using the eddy current sensor to obtain a reference high value from the signal, which is measured when the eddy sensor current is off-wafer or when the substrate is a bare substrate;

using the eddy current sensor to obtain a reference low value from the signal, which is measured when the substrate has the particular thickness; and processing the values to effect calibration.

20. The method of claim 19, wherein processing includes:
calculating a slope as a ratio of a first difference and a second difference, the first difference being between the setpoint high value and the setpoint low value and the second difference being between the reference high value and the reference low value; and calculating an offset as the setpoint low value.

21. The method of claim 20, wherein processing further includes:
applying the slope and the offset to the signal.

22. The method of claim 12, wherein:
the signal is a phase signal or an amplitude signal.

* * * * *